United States Patent [19]

Myers et al.

[11] Patent Number: 4,760,083
[45] Date of Patent: Jul. 26, 1988

[54] 3,3-DISUBSTITUTED INDOLINES

[75] Inventors: Melvyn J. Myers; Victor J. Nickolson, both of Wilmington, Del.

[73] Assignee: E. I. Dupont de Nemours & Company, Wilmington, Del.

[21] Appl. No.: 944,953

[22] Filed: Jan. 5, 1987

Related U.S. Application Data

[63] Continuation-in-part of Ser. No. 850,015, Apr. 10, 1986, abandoned.

[51] Int. Cl.[4] .................. C07D 209/34; A61K 31/40
[52] U.S. Cl. ............................ 514/333; 544/216; 544/238; 544/296; 544/333; 544/336; 544/357; 546/256
[58] Field of Search ............... 546/256, 273; 514/333, 514/339

[56] References Cited

U.S. PATENT DOCUMENTS

| 3,574,232 | 4/1971 | Canas-Rodriguez et al. | 260/326.11 |
| 4,273,860 | 6/1981 | Adin | 430/338 |
| 4,372,960 | 2/1983 | L'Italien | 424/267 |
| 4,434,169 | 2/1984 | Poschel et al. | 424/263 |
| 4,452,990 | 6/1984 | Butler | 548/543 |

FOREIGN PATENT DOCUMENTS 0005143 11/1979 European Pat. Off.
55-129284 10/1980 Japan.

OTHER PUBLICATIONS

Abstract of Japan 59-098896A; Nippon Telegraph & Telephone, (Original Patent Dated Jun. 7, 1984).
Adin, et al.; Research Disclosures, 184, (1979), pp. 446–454.
Daisley, et al.; J. Heterocyclic Chem., 19, (1982), pp. 1013–1016.
Ogata, et al.; Eur. J. Med. Chem., Chem. Ther., (1981), 16(4), pp. 373–378.

Primary Examiner—Joseph Paul Brust
Attorney, Agent, or Firm—Robert W. Black

[57] ABSTRACT

Cognitive deficiencies and/or neurological function deficits and/or mood and/or mental disturbances are treated by the administration of 3,3-disubstituted indolines. The indolines have the formula:

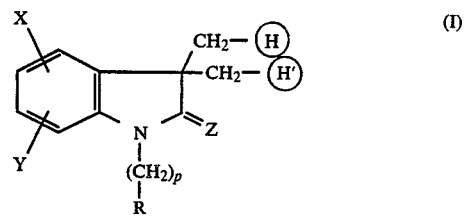

wherein:
p is 0 or 1;
Z is O or S;
R is $C_1$–$C_{10}$ alkyl, $C_3$–$C_8$ cycloalkyl, 2-pyridyl, 3-pyridyl, 4-pyridyl or

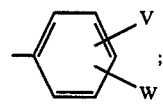

V, W, X, and Y independently are H, halo, $C_1$–$C_3$ alkyl, $OR^1$, $NO_2$, $CF_3$, CN or $NR^2R^2$;
$R^1$ and $R^2$ independently are H or $C_1$–$C_3$ alkyl;
—(H) and —(H') independently are 6-membered heterocyclic aromatic rings containing at least one nitrogen atom as a part of the ring optionally substituted with one substituent selected from the group $C_1$–$C_3$ alkyl, halo, $OR^1$ or $NR^1R^2$; or an N-oxide or pharmaceutically suitable acid addition salt thereof.

36 Claims, No Drawings

3,3-DISUBSTITUTED INDOLINES

RELATED APPLICATIONS

This application is a continuation-in-part of copending U.S. Ser. No. 850,015, filed Apr. 10, 1986, now abandoned.

BACKGROUND OF THE INVENTION

1. Field of Invention

This invention relates to indolines and more particularly to 3,3-heterocyclic-disubstituted indolines, pharmaceutical compositions containing them, processes for preparing them and methods of using them in mammals to treat cognitive deficiencies and/or neurological function deficits and/or mood disturbances such as found, for example, in degenerative nervous system diseases.

2. Background Including Prior Art

There is a steadily growing need for effective treatment for Nervous System Disorders causing cognitive and neurological deficiencies. Many of these diseases, of which the incidence generally rises with increasing age, are due to degenerative changes in the nervous system. Although in early stages of some diseases certain systems are rather specifically affected (e.g. cholinergic systems in Alzheimer's Disease, and Myasthenia Gravis, the dopaminergic system in Parkinson's Disease, etc.), multiple neurotransmitter system deficiencies (acetylcholine, dopamine, norepinephrine, serotonin) are generally found at later stages of these diseases and are thought to exist at all stages of diseases such as senile dementia, multi-infarct dementia, Huntington's disease, mental retardation, etc. This may explain the generally observed multiple symptomatology which includes cognitive, neurological and affective/psychotic components (see Gottfries, *Psychopharmacol.* 86, 245, 1985). Deficits in the synthesis and release of acetylcholine in the brain are generally thought to be related to cognitive impairment (see Francis et al., *New England J. Med.*, 313, 7, 1985) whereas neurological deficits (e.g., Parkinson Symptoms) and mood/mental changes may be related to impairment of dopaminergic and serotonergic systems, respectively. Other neurological deficits (e.g., Myasthenia Gravis) are related to cholinergic deficiencies in the peripheral nervous system.

Treatment strategies employed hitherto encompass vasoactive drugs like vincamine and pentoxifylline; "metabolic enhancers" like ergoloid mesylates, piracetam and naftidrofuryl; neurotransmitter precursors like 1-DOPA, choline and 5-hydroxytryptamine; transmitter metabolizing enzyme inhibitors like physostigmine; and neuropeptides like adrenocorticotropic hormone and vasopressin-related peptides. Except for 1-DOPA treatment in Parkinson's disease and cholinesterase inhibitor treatment in Myasthenia Gravis, these treatment strategies have generally failed to produce clinically significant improvements (Hollister, *Drugs*, 29, 483, 1985). Another strategy to treat these multiple symptoms is to enhance the residual function of the affected systems by enhancing the stimulus-induced release of neurotransmitters. Theoretically, such an enhancement would improve the signal-to-noise ratio during chemical transmission of information, thereby reducing deficits in processes related to cognition, neurological function and mood regulation.

To date, there are not many patent or literature references which describe 3,3-heterocyclic disubstituted indolines. Most pertinent, are Japanese Patent No. 55-129284, issued Oct. 6, 1980 and M. Ogata et al., *Eur. J. Med. Chem-Chim. Ther.*, 16(4), 373–378 (1981), which describe antifungal compounds having the formula:

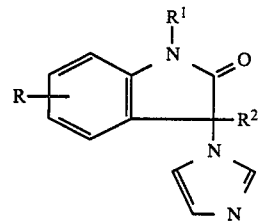

wherein
R is H, halogen, alkyl, or alkoxy;
$R^1$ is H, alkyl, aryl or acyl; and
$R^2$ is thienyl, or imidazole, amongst non-heterocyclic groups.

R. W. Daisley, et al., *J. Heterocyclic Chem.*, 19, 1913–1016, (1982), report 1-methyl-3,3-dipiperidinoindol-2-(3H)-one as product from the reaction of the corresponding (Z) or (E) 2-arylmethylidene-indol-3(2H)-one with ethyl cyanoacetate in the presence of excess piperidine. No utility for the compound is described.

Japanese Patent No. 59-98896 describes high sensitivity, high stability recording medium containing a 3,3-disubstituted-2-oxo-2,3-dihydroindole derivative of the formula shown below as a near infrared absorber.

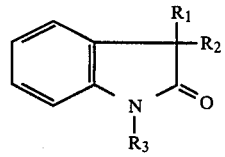

wherein
$R_1$, $R_2$, same or different, are a saturated heterocyclic ring including morpholino, pyrrolidinyl, amongst others containing at least one nitrogen atom; and
$R_3$ is H or alkyl.

3,3-bis(morpholino)oxoindole is also disclosed in U.S. Pat. No. 4,273,860, to A. Adin, June 16, 1981 and in A. Adin, et al., *Research Disclosures*, 184, 446–454 (1979), as a destabilizer material in a photoinhibitor composition utilizing cobalt (111) complexes.

The above references, other than J55-129284, and M. Ogata et al., *Eur. J. Med. Chem-Chim. Ther.*, 16(4), 373–378 (1981) all describe 3,3-disubstituted indolones wherein the heterocyclic groups are both saturated rings. In all of the above references, the heterocyclic ring is attached to the indoline by a ring nitrogen. Furthermore in the references other than J55-129284, there is no suggestion of pharmaceutical utility for these 3,3-disubstituted indolines.

SUMMARY OF THE INVENTION

It has now been found that compounds of Formula (I) enhance the stimulus-induced release of neurotransmitters, specifically acetylcholine and, in addition, dopamine and serotonin in nervous tissue and improve processes involved in learning and memorization of an active avoidance task.

More particularly, according to the present invention there is provided a pharmaceutical composition comprising a suitable pharmaceutical carrier and a therapeutically effective amount of a compound having the formula:

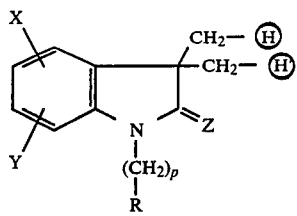

wherein:
p is 0 or 1;
Z is O or S;
R is $C_1-C_{10}$ alkyl, $C_3-C_8$ cycloalkyl, 2-pyridyl, 3-pyridyl, 4-pyridyl or

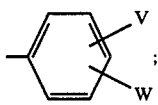

V, W, X, and Y independently are H, halo, $C_1-C_3$ alkyl, $OR^1$, $NO_2$, $CF_3$, CN or $NR^1R^2$;
$R^1$ and $R^2$ independently are H or $C_1-C_3$ alkyl;
—Ⓗ and —Ⓗ independently are 6-membered heterocyclic rings containing at least one nitrogen atom as a part of the ring optionally substituted with one substituent selected from the group $C_1-C_3$ alkyl, halo, $OR^1$ or $NR^1R^2$; or
an N-oxide or pharmaceutically suitable acid addition salt thereof.

Also provided is a method for the treatment of a cognitive deficiency and/or neurological function deficit and/or mood/mental disturbance such as found for instance in degenerative nervous system disease in a mammal, said method comprising administering to the mammal a therapeutically effective amount of at least one of the above-described compounds of Formula (I).

Additionally provided is a novel class of compounds of Formula (I) active in treating cognitive and/or neurological deficiencies and/or mood/mental disturbances such as found, for instance in degenerative nervous system disease.

Further provided is a process for preparing a compound of Formula (I) comprising
(a) contacting an oxindole of the formula

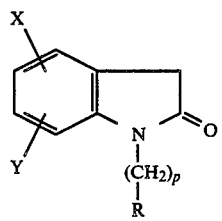

wherein p, X, Y, and R are as defined above, with a base;
(b) contacting the product of step (a) with a compound of the formula D—CH₂—Ⓗ wherein —Ⓗ is as defined above and D is a halide, methanesulfonate, or p-toluenesulfonate;
(c) contacting the product of step (b) with a compound of the formula D—CH₂—Ⓗ′ wherein —Ⓗ′ is defined above and D is a halide, methanesulfonate, or p-toluenesulfonate; and
(d) optionally contacting the product of step (c) with Lawesson's reagent or with $P_4S_{10}$ to prepare the thiooxindole.

PREFERRED EMBODIMENTS

Preferred compounds are those of formula (I) where:
p is 0; or
Z is O; or
X and Y are H; or
R is $CH_3$, phenyl or m-chlorophenyl; or
—Ⓗ and —Ⓗ′ are each pyridyl attached by a ring carbon atom.

Specifically preferred for their ability to enhance stimulus-induced acetylcholine release are:
3,3-Bis(2-pyridylmethyl)-1-phenylindolin-2-one;
3,3-Bis(3-pyridylmethyl)-1-phenylindolin-2-one;
3,3-Bis(4-pyridylmethyl)-1-phenylindolin-2-one;
3,3-Bis(4-pyridylmethyl)-1-methylindolin-2-one;
3,3-Bis(4-pyridylmethyl)-1-(3-chlorophenyl)indolin-2-one;

and pharmaceutically suitable acid addition salts thereof.

DETAILED DESCRIPTION OF THE INVENTION

Synthesis

Most of the oxindole compounds of this invention are prepared by the synthetic sequence represented by Scheme 1.

Scheme 1

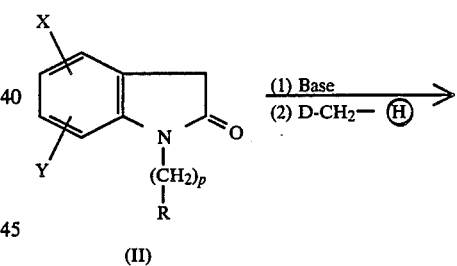

(II)

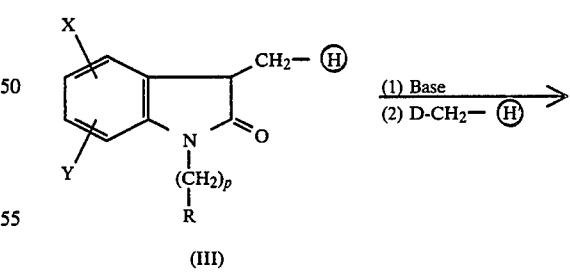

(III)

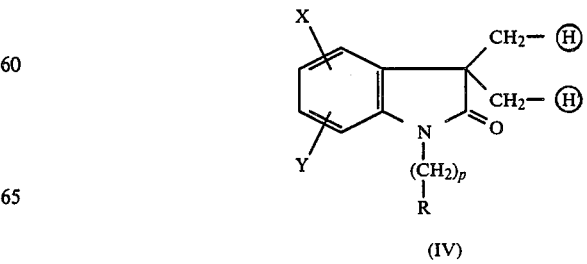

(IV)

X, Y, p, R, —Ⓗ, and —Ⓗ are as defined above, D represents a displaceable group such as halogen (I, Br, Cl, or F) or methanesulfonate or p-toluenesulfonate. These reactions result from formation of an anion at the 3-position of the oxindole of Formula (II) by reaction of the oxindole with a suitable base followed by displacement of D by the anion and formation of the 3-mono-substituted compound (III). This mono-substituted product (III) can then either be isolated prior to the next step or, preferably, especially when —Ⓗ and —Ⓗ are the same, treated again with another equivalent of base without prior isolation, to give the 3,3-disubstituted oxindole (IV).

Suitable bases for forming the anion include sodamide, lithium diisopropylamine, sodium hydride, potassium tert-butoxide, sodium alkoxide, potassium alkoxide, lithium alkoxide, potassium hydride, lithium 2,2,6,6-tetramethylpiperidide, butyl lithium, sec-butyl lithium, tert-butyl lithium, and lithium, sodium or potassium hexamethyldisilazide. The reaction is run in an aprotic solvent, generally in an ether such as diethylether, glyme, tetrahydrofuran or dioxane. However, if the oxindole is soluble in a nonpolar solvent, the reaction may be run in a hydrocarbon such as hexane, heptane, cyclohexane, methylcyclohexane, benzene or toluene.

In running the reaction, the oxindole is dissolved in an appropriate solvent, and, depending upon the strength of the base, the solution is cooled to a temperature between −40° C. and room temperature. When a more reactive base such as lithium diisopropylamide (LDA) is used, the solution is cooled to a temperature of −30° C. and a solution of the LDA in an appropriate solvent, such as tetrahydrofuran, is added dropwise over a period of 15 minutes to one hour, while maintaining the temperature at approximately −30° C.

If one chooses to use sodamide instead of LDA, benzene is the preferred solvent. The sodamide is added to a solution of the indolinone in benzene at room temperature. In order to drive the reaction to completion, the solution is refluxed until ammonia can no longer be detected evolving from the reaction.

A solution of the electrophile D—CH₂—Ⓗ is then added to the indolinone anion. Again, if a very reactive base such as LDA is used to generate the anion, the reaction is cooled to −30° C. and the electrophile is added dropwise. If a less active base is used to generate the anion, the electrophile is added at a temperature between 0° C. and room temperature and then the reaction mixture is refluxed.

The bisubstituted product (IV) can be prepared by generation of a second anion at the three position of the indolinone. The anion formation followed by alkylation can be done in the same manner as described above for the preparation of a mono-substituted compound of Formula (III).

Instead of running the reaction sequentially, one may at times, add two equivalents of base to the indolinone, followed by two to three equivalents of the alkylating agent. In some cases, especially those where —Ⓗ is the same as —Ⓗ, it may be convenient to accomplish alkylation of the oxindole under phase transfer conditions, e.g., using a base such as sodium hydroxide dissolved in water, a wate immiscible solvent such as benzene or toluene, a phase transfer catalyst such as benzyltriethylammonium chloride and two molar equivalents of the alkylating agent D—CH₂—Ⓗ. Under such conditions, vigorous stirring and elevated reaction temperatures, e.g., 60°-80° C., may facilitate conversion to the 3,3-dialkylated oxindole.

When the reaction is complete as evidenced by thin layer chromatography, excess anion is decomposed with saturated ammonium chloride solution, and the reaction is taken through an acid-base cycle to remove neutral starting materials. Purification of the basic product generally involves conventional purification techniques such as flash chromatography followed by re-crystallization if necessary. The pure base (one spot on thin layer chromatography and analytical HPLC) is converted to the dihydrochloride by adding a slight excess of 25% hydrochloric acid in a solvent such as ethanol. Generally, adding an equal volume of acetone to the boiling solution affords a crop of pure colorless crystals upon cooling. Other methods that will be obvious to one skilled in the art can be used to obtain a crystalline product. The hydrochloride salt can be re-crystallized from isopropanol, 1-propanol, ethanol, 95% ethanol, methanol, or mixtures of an alcohol with acetone, ethyl acetate, isopropyl acetate, or acetonitrile.

The hydrochloride salt can be converted to the corresponding free base by treatment with an inorganic base, e.g., sodium hydroxide, potassium hydroxide, sodium phosphate, ammonium hydroxide, or potassium carbonate, and then can be taken up in an organic solvent such as methylene chloride, ether, or ethyl acetate, and re-precipitated as a salt with some other pharmacologically acceptable acid such as maleic acid, methanesulfonic acid, napthalene-2-sulfonic acid, tartaric acid, hydrogen bromide, etc.

Alternatively, thallium (I) ethoxide can be used as the base as illustrated by Scheme 2. The indolinone is dissolved in a suitable solvent, preferably warm benzene, and an equimolar quantity of thallium (I) ethoxide is added rapidly to it. The organothallium compound (V) which precipitates out as a poisonous, yellowish, crystalline stable solid, is filtered affording the thallium compound in yields of 85-95%. Care must be exercised in handling thallium compounds because of their toxicity.

Scheme 2

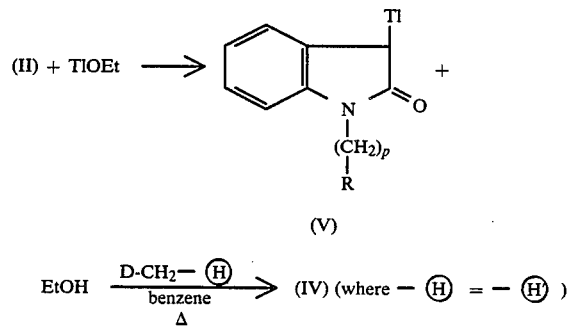

Organothallium compounds generally react with electrophiles to form the monoalkylated products. However, with very reactive electrophiles such as picolyl chlorides, benzyl bromide or the like, the 3,3-bis-alkylated products are obtained, as shown in Scheme 2, and as is exemplified by Example 1.

The thallium indoline (V) is heated with an electrophile such as picolyl chloride in an inert solvent, such as benzene or toluene, at 30° C. to the boiling point of the solvent, for several hours to 24 hours. Preferred is a temperature of 80° C. for 24 hours. When the reaction is complete as indicated by thin layer chromatography and the precipitated thallium chloride is filtered off, the remaining organic solution is taken through an acid-base cycle and purification, and optional salt formation is carried out as described above.

Preparation of the starting oxindole (II) represented in Scheme I and Scheme 2 can be carried out by one or more of a large number of general synthetic methods described in the chemical literature. For instance the reaction of an N-substituted aniline (VI) with chloroacetyl chloride to form an amide (VII) is a well known reaction. This is illustrated in Scheme 3.

Scheme 3

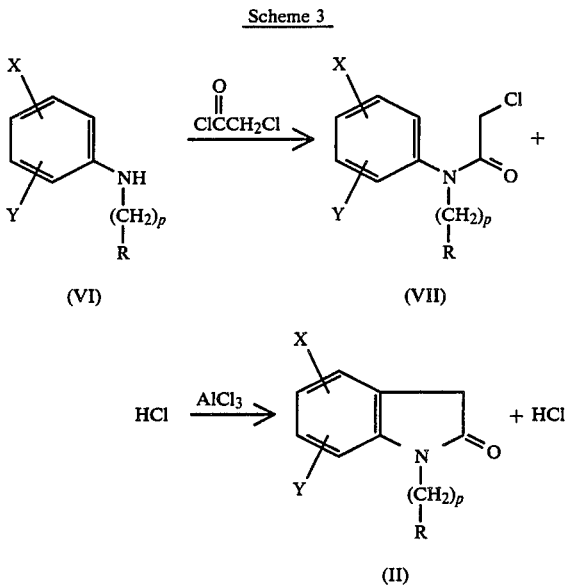

Requisite diarylamine syntheses (VI; where p=0, R=substituted phenyl) are widely known in the chemical literature. Many involve conversion of N-aryl-phenylenediamine by diazotization and for example Sandmeyer reaction with the appropriate substituted diarylamine. Again, one skilled in the art of organic synthesis can select a suitable synthesis for preparation of the appropriate diarylamine required to extend the Examples to the related compound of this invention. Recent useful syntheses include those described by Katritzsky et al., *J. Chem. Soc., Perkin. Trans. I*, 2611 (1983), Gorwin et al., *Chem. Commun.,* 4, 238 (1985), and Malz et al. in U.S. Pat. No. 4,431,841A (1984).

Other N-substituted anilines (VI; where p=1) can be made by conventional synthetic methods commonly used in organic chemistry, e.g., by reaction of a suitable carboxylic acid chloride with an aniline to afford an amide which is then reduced by lithium aluminum hydride or diborane in tetrahydrofuran at about 67° C. to afford the N-substituted aniline (VI), as depicted in Scheme 4 below.

Scheme 4

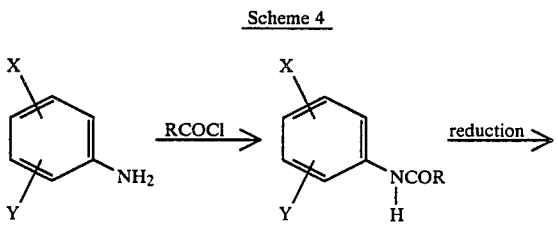

-continued
Scheme 4

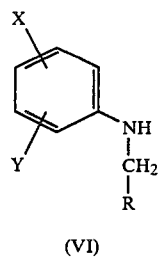

(VI)

(where p = 1)

The starting oxindole (II) can then be prepared by Friedel-Crafts ring closure of an amide of Formula (VII) in the presence of a Lewis acid such as aluminum chloride (AlCl₃). Other Lewis acids such as tin tetrachloride (SnCl₄) or boron trifluoride (BF₃) can be used depending on the chemical structure of the amide (VII). Choice of solvent if any is dependent on the actual compound of Formula (VII) to be cyclized and on the Lewis acid used. Nitrobenzene, tetrachloroethane, ethylene dichloride and methylene chloride are often used as solvents. Generally, the use of AlCl₃ without a solvent is preferred.

If substituents X and Y are electron withdrawing and deactivate the aromatic ring to which they are attached towards electrophilic substitution and if V and W are electron donating or activate the ring (where R is substituted phenyl) other methods may be more convenient for synthesis of oxindoles (II). These methods will be known to one skilled in the art of organic synthesis who is familiar with the literature of oxindole synthesis.

For example, in addition to the Friedel-Crafts cycloalkylation illustrated by Scheme 2, X and Y substituted oxindoles can be made by the general "azasulfonium ion" rearrangement methods of Gassman [U.S. Pat. Nos. 3,897,451 (1975), 3,996,264 (1976), and 3,972,894 (1976); see also *J. Am. Chem. Soc.*, 96, 5512 (1974) etc.] or in some instances from o-nitrophenyl acetic acid [see Walker, *J. Am. Chem. Soc.*, 77, 3544 (1955) and Hardigger et al., *Helv. Chim. Acta.*, 39, 514 (1956)].

Other more direct synthesis of 3,3-disubstituted 2-oxindoles can be carried out by use of the Brunner reaction of N-arylhydrazides [Org. Synthesis, 37, 60 (1957); Rohrscheidt et al., *Liebigs Ann. Chem.*, 680 (1978)] and by processes involving direct oxidation of substituted indoles [Lawson et al., *J. Org. Chem.*, 26, 263 (1961); R. L. Hinman et al., ibid, 29, 1206 (1964); Lawson et al., *J. Am. Chem. Soc.*, 82, 5918 (1960); Szabo-Pusztag et al., *Synthesis,* 276 (1979)]. Other methods for making oxindoles are described by A. P. Kozikowsi, et al., *J. Am. Chem. Soc.*, 43 (10), 2083 (1978); T. Nakashima, et al., *Chem. Pharm. Bull.*, 17 (11), 2293 (1969); Y. Tamura, et al., *Synthesis,* 534 (1981); J. F. Bunnett, *J. Org. Chem.*, 28 (1), 1 (1963); R. R. Goehring, *J. Am. Chem. Soc.*, 107 (z), 435 (1985); T. Hamada, et al., *Chem. Pharm. Bull.*, 29 (1), 128 (1981); D. Ben-Ishai, et al., *Tet. Lett.*, 21 (6), 569–72 (1980); J. F. Wolfe, *J. Am. Chem. Soc.*, 102 (10), 3646 (1980); J. G. Atkinson, *Tet. Lett.*, (31), 3857 (1979); M. Mori, et al., *Tet. Lett.*, (21) 1807 (1976); P. Parimoo, *Indian J. Chem.*, 10 (17), 764 (1972); D. Klamann, et al., *Chem Ber.*, 100 (6), 1870 (1967).

This bibliographic list is intended to be illustrative of the great variety of methods available to make the 2-oxindole intermediates useful in this invention.

The 2-thiooxindoles (VIII) of this invention can be made by reaction of the oxindoles with Lawesson's reagent or with phosphorus pentasulfide (P$_4$S$_{10}$) as is illustrated in Scheme 5.

Scheme 5

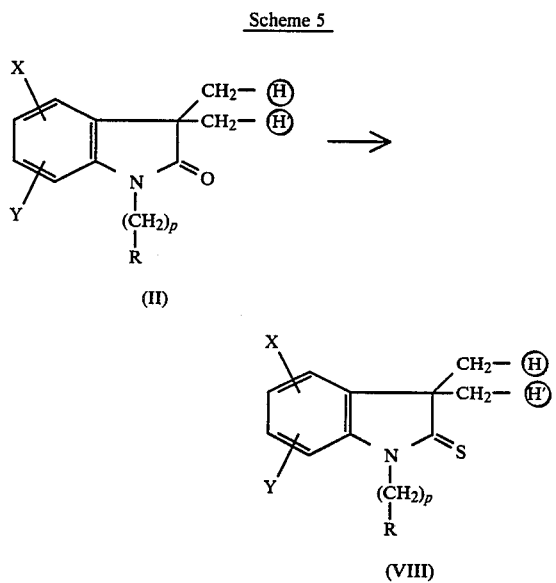

Lawesson reagent is 2,4-bis(4-methoxyphenyl)-1,3-dithia-2,4-diphosphetane-2,4-disulfide. Its use in the thiation of carboxamides and lactams is well known, as is the use of phosphorus pentasulfite for similar reactions. The reactions are customarily carried out in methylene chloride, benzene, acetonitrile, or piperidine depending on the solvent power and reaction temperature required for the particular oxindole involved. Usually the P$_4$S$_{10}$ works better if it is first purified by extraction into methylene chloride by Soxhlet extraction. Ordinarily thiation reactions can be carried out at mild temperatures (25°–80° C.) and the products can be isolated by chromatography or crystallization.

The nitrogen-containing heterocyclic compounds D—CH$_2$—Ⓗ used as intermediates in Schemes 1 and 2 are available by methods described in standard works on heterocyclic chemistry such as Katritzsky and Rees, Comprehensive Heterocyclic Chemistry, Vols. 2–5, Pergamon Press, N. Y., 1984. In some instances the preparation of the corresponding hydroxy compounds (D=OH) is described in the literature; these can be converted to the corresponding halo compounds (e.g. D=Br) for the alkylation reaction indicated in Schemes 1 and 2 by mild reagent (such as Ph$_3$P,CBr$_4$). Alternatively the hydroxy compounds can be converted to the corresponding sulfonate esters (e.g. D=CH$_3$SO$_2$O) by reaction with the corresponding sulfonylchloride in the presence of pyridine or triethylamine at cold temperatures. Generally, temperatures of about 0° C. to −20° C. are preferred for formation of these sulfonates.

The compounds useful in the present invention can be used as their free base or their pharmaceutically suitable salts. Salt formation is well known to those skilled in the art.

The invention can be further understood by the following examples in which parts and percentages are by weight unless otherwise indicated; all temperatures are in degrees centigrade.

EXAMPLE 1

3,3-Bis(2-pyridylmethyl)-1-phenylindolin-2-one

To a solution of 0.1 mole of N-phenylindolin-2-one in 200 ml of benzene under N$_2$ was rapidly added 0.1 mole of thallium ethoxide. The solution was heated briefly to boiling. At about 50°, a heavy precipitate started to form. After refluxing for 5 minutes, the mixture was cooled and 200–300 ml of hexane was added to complete precipitation. The solid was filtered off and dried to yield 85% of the thallium salt of N-phenylindolin-2-one as a yellow solid.

0.22 Mole of picolylchloride hydrochloride was carefully converted to the free base by dissolving in 30 ml cold water, cooling to 0°–5° and basifying with ammonium hydroxide. The free base was extracted out (3×100 ml benzene), dried with Na$_2$SO$_4$ and filtered, while maintaining the temperature no higher than 10°.

To this solution was added the thallium salt of the N-phenylindolin-2-one, followed by 200 ml benzene. This mixture was refluxed overnight and after cooling, the precipitated thallium chloride was filtered off. The basic product was extracted out of the filtrate with 0.5N hydrochloric acid and was then reconverted to the base with ammonium hydroxide and extracted into methylene chloride, dried with anhydrous potassium carbonate, filtered and evaporated. The remaining thick dark red oil was dissolved in 50 ml ether and trituration with a glass rod started crystallization, which was complete in a short while. The solid was filtered off, washed with ether and dried to yield 11.2 g of product; m.p. 107°–111°. The product was purified by flash chromatography using 40–60 micron silica gel 60 (E. Merck) on a column 10" long×2" in diameter. Elution with 95:5 methylene chloride-methanol (detection with a 256 μm Gow-Mac detector) afforded 8.2 g of pure free base in fractions 5 through 10 (100 ml each), R$_f$0.33 (silica gel; 95:5 methylene chloride/methanol); m.p. 129°–130°.

Anal. Calcd. for C$_{26}$H$_{21}$N$_3$O: C, 79.77; H, 5.41; N, 10.73. Found C, 80.05; H, 5.65; N, 10.67.

EXAMPLE 2

3,3-Bis(2-pyridylmethyl)-1-phenylindolin-2-one dihydrochloride 8.2 g of 3,3-Bis(2-pyridylmethyl)-1-phenylindolin-2-one was converted to the dihydrochloride salt by dissolving it in 25 ml methylene chloride and adding 25 ml of 25% hydrochloric acid in ethanol. The solution was evaporated and the glassy residue was dissolved in 75 ml boiling acetone. Cooling to room temperature and trituration started crystallization. After sitting at room temperature for 6 hours, the mixture was kept at 0° overnight. The product was then filtered, washed with cold acetone and dried in a vacuum oven for 1 hour at 60° over Granusic to yield 8.55 g; m.p. 250°–251°. The product was recrystallized from isopropanol affording 8.29 g; m.p. 250°–251°.

EXAMPLE 3

3,3-Bis(3-pyridylmethyl)-1-phenylindolin-2-one dihydrochloride

To 0.3 mole of N-phenylindolinone in 300 ml of benzene was added 0.36 mole of sodamide in one batch. The mixture was refluxed for 3 hours (until ammonia evolution ceases), and the reaction was then cooled to room temperature. 0.5 Mole of 3-picolylchloride was carefully prepared from the hydrochloride salt in the same manner previously described for 2-picolylchloride and was then extracted into benzene, dried with sodium sulfate and filtered. This benzene solution of 3-picolylchloride was added dropwise with vigorous mechanical stirring to the N-phenylindolinone anion solution under nitrogen over a period of 30 minutes at 20°. After completion of addition, the reaction was refluxed for an additional 3 hours.

The reaction mixture was cooled to room temperature and a second portion of 0.36 mole of sodamide was added in one batch. As above, the mixture was refluxed until ammonia evolution from the reaction ceased (3 hours).

The reaction mixture was cooled to room temperature and an additional 0.5 mole of 3-picolylchloride base in benzene was added dropwise with vigorous stirring to the indolinone anion solution over a period of 30 minutes at 20°. After completion of addition of the 3-picolylchloride, the reaction mixture was refluxed 3 hours. The reaction mixture was then cooled in an ice bath and 1N HCl was added (300 ml) in conjunction with vigorous mechanical stirring. The HCl phase was separated and the organic phase was extracted twice more with 100 ml of 1N HCl. The combined acid extracts were made basic, extracted with methylene chloride, washed with water, dried with sodium sulfate, filtered and evaporated. The dark oil was triturated with ether to yield a crop of dense crystals, which were filtered, washed with ether until the washings were colorless, to afford 3.1 g of solid; m.p. 136.5°-138°. A portion (2.8 g) was dissolved in 10 ml of 25% hydrochloric acid in ethanol. Scratching started crystallization (dense crystals). After one hour at 0°, the white crystals were filtered off and dried to yield 3.2 g of the title compound; m.p. 156°. The product was dissolved in 115 ml boiling ethanol, to which 10 ml of boiling acetone was carefully added. The solution was allowed to cool undisturbed for 8 hours, then overnight at 0°. The pure white crystals were filtered, washed with cold 1:1 ethanol-acetone and dried under infrared lamps, to afford 2.6 g of pure product; mp 156°-156.5°.

EXAMPLE 4

3,3-Bis(4-pyridylmethyl)-1-phenylindolin-2-one dihydrochloride

N-phenylindolinone (0.05 mole) was dissolved in the minimum amount of dry tetrahydrofuran in a multineck flask under $N_2$. Lithium diisopropylamide (0.05 mole) was weighed out in a dry box into a dropping funnel and then dry tetrahydrofuran was added to the lithium diisopropylamide to dissolve it. The dropping funnel containing the lithium diisopropylamide-tetrahydrofuran solution was sealed and removed from the dry box. The indolinone solution was cooled to −30° and the lithium diisopropylamide solution was added to it dropwise at −30° over a period of 15 minutes. After the addition, the reaction was allowed to warm to room temperature. The reaction mixture was again cooled to −30° and 4-picolylchloride (0.06 mole), which had been converted to the free base as previously described and then dissolved in 25 ml tetrahydrofuran, was added dropwise during 30 minutes at −30°.

After completion of addition, the reaction was allowed to warm to room temperature for 30 minutes. It was then cooled to −30° and the second portion of lithium diisopropylamide (0.05 mole) in tetrahydrofuran was added dropwise over a period of 15 minutes at −30°. After completion of addition, the reaction mixture was allowed to warm to room temperature as a second batch of 4-picolylchloride hydrochloride (0.06 mole) was converted to the free base.

The room temperature anion reaction mixture was again cooled to −30° and the second portion of 4-picolylchloride in 25 ml tetrahydrofuran was added dropwise over a period of 30 minutes at −30°. The reaction mixture was brought to room temperature and maintained at room temperature for 1-17 hours depending on convenience. Any remaining anion was destroyed by carefully adding 50 ml saturated ammonium chloride solution. The tetrahydrofuran was then evaporated and the residue was dissolved in methylene chloride and extracted out of the methylene chloride with 3×100 ml portions of 0.5N hydrochloric acid. The combined HCl portions were made basic (pH=12) and product extracted with (3×100 ml) methylene chloride. The methylene chloride was dried with sodium sulfate, filtered and evaporated to yield 20 g of product. Purification by chromatography in 10 g batches (40-63 μm silica gel on a column 8" long×2" diameter; eluting with: EtOAc 69.46%, Hexane 29.75%, and Et₃N 0.79%) gave 19.2 g of the base (93%); m.p. 186.0°-186.5°.

3,3-Bis(4-pyridylmethyl)-1-phenylindolin-2-one (19 g) was converted to the dihydrochloride by treatment with 40 ml 25% hydrochloric acid in ethanol. To the mixture was added 50 ml isopropanol and the solution was heated to boiling. Boiling acetone was added until thick needles just started to form (total volume of solvents: 200-250 ml). The solution was allowed to cool to room temperature, then allowed to stand overnight at 0°. The solid was filtered and washed with cold isopropanol to yield 19.5 g (84%) of the title compound; m.p. 257°-8°. (Note: degree of drying has an effect on m.p. of the dihydrochloride; very slowly increasing the temperature of the melting point apparatus gives a melting point of 275°-276°). A second crop was obtained by evaporating the filtrate, dissolving the residue in isopropanol and adding approximately an equal volume of acetone; the mixture was allowed to sit overnight at room temperature, and then 6 hours at 0° C. to yield an additional 2.8 g, m.p. 252°-253°. Recrystallization yielded 2.4 g, of the second crop: m.p. 257°-258° C. The total dihydrochloride yield was 21.9 g (94%).

EXAMPLE 5

3,3-Bis(4-pyridylmethyl)-1-methylindolin-2-one dihydrochloride

To a solution of 0.05 mole of 1-methylindolin-2-one in 50 ml of tetrahydrofuran cooled to −30° was added 0.1 mole of lithium diisopropylamide in 100 ml of tetrahydrofuran in a dropwise fashion over 30 minutes. The reaction mixture was allowed to warm to room temperature after completion of addition, and was then cooled back down to −30°. Following the careful conditions described previously for the conversion of picolylchloride hydrochloride to picolylchloride base, 0.21 mole of 4-picolylchloride hydrochloride was converted to the anhydrous free base and was then dissolved in tetrahydrofuran (150 ml). This solution was added dropwise during 60 minutes at −30° to the reaction mixture.

After completion of addition, the reaction mixture was allowed to warm to room temperature for one hour, then was cooled and carefully decomposed by the dropwise addition of saturated ammonium chloride.

When the addition was complete, the tetrahydrofuran was evaporated and the residue was partitioned between benzene and 0.5N HCl. This residue was transferred to a separatory funnel and the organic phase was extracted twice more with 0.5N HCl. The combined acid extracts were basified, extracted with benzene, dried with Na$_2$SO$_4$, filtered and evaporated. The residue was triturated with ether, filtered and washed with a small amount of ether to yield 2.9 g; m.p. 149.9°–150.9°. This product was converted to the dihydrochloride salt with 25% hydrochloric acid and ethanol and crystallized from ethanol-acetone to yield 1.9 g of the title compound, m.p. 274.5°.

EXAMPLE 6
3,3-Bis(4-pyridylmethyl)-1-(3-chlorophenyl)indolin-2-one dihydrochloride Using the procedure of Example 3, the title compound was prepared from N-(3-chlorophenyl)indolin-2-one in a yield of 24%, m.p. 275°–276° C.

EXAMPLES 7 AND 8
3,3-Bis(4-pyridylmethyl-1-oxido)-1-phenylindolin-2-one and
3-(4-pyridylmethyl)-3-(4-pyridylmethyloxido)-1-phenylindolin-2-one A solution of 4.14 g (0.024 mole) of 80–85% m-chloroperbenzoic acid in 50 ml methylene chloride was added dropwise with magnetic stirring to 3,3-bis(4-pyridylmethyl)-1-phenylindolin-2-one in 100 ml methylene chloride, and solution was stirred overnight. Checking for peroxide with moist starch iodide paper was negative, so the methylene chloride solution was washed with 3×75 ml 5% sodium bicarbonate, dried with sodium sulfate, filtered and evaporated.

The residue was triturated with 5:1 ether/ethyl acetate to yield 2.14 g of a solid containing the bis-N-oxide, the mono-N-oxide, and a small amount of starting material. The reaction mixture was purified by flash chromatography (silica gel, 40–63 μm, eluting with 90:10 chloroform/methanol) affording 1.18 g, of the major product, R$_f$=0.34; m.p. 265.3°–265.7° (after recrystallization from 10 ml water). The high resolution mass spectrum confirmed the major product as the bis N-oxide; m/e 423.1595 (M+, calcd. for C$_{26}$H$_{21}$N$_3$O$_3$ 423.1582).

A second fraction (200 mg) obtained from the flash chromatography was identified as the mono-N-oxide; 3-(4-pyridylmethyl)-3-(4-pyridylmethyloxido)-1-phenylindolin-2-one, R$_f$=0.41; m.p. 217.7°–218.5°.

Mass spectrum m/e 407.1631 (M+, calcd. for C$_{26}$H$_{21}$N$_3$O$_2$ 407.1634).

The compounds of Examples 1–8, and other compounds which can be prepared by such procedures and procedures described in the synthesis disclosure are illustrated by the structures represented in Table 1. This Table is intended to illustrate the invention, but not to limit its breadth.

TABLE 1

| Ex. No. | X | Y | R | V | W | p | —(H) | —(H) | Z | m.p. °C. |
|---|---|---|---|---|---|---|---|---|---|---|
| 1 | H | H | phenyl (V,W) | H | H | 0 | 4-pyridyl | 4-pyridyl | O | 129–130 |
| 2 | H | H | phenyl (V,W) | H | H | 0 | 4-pyridyl | 4-pyridyl | O | 250–251 (2 HCl) |
| 3 | H | H | phenyl (V,W) | H | H | 0 | 3-pyridyl | 3-pyridyl | O | 156–156.5 (2 HCl) 136.5–138 (free base) |
| 4 | H | H | phenyl (V,W) | H | H | 0 | 4-pyridyl | 4-pyridyl | O | 257–258 (2 HCl) 186–186.5 (free base) |

TABLE 1-continued

General structure: indolin-2-one with X, Y substituents on benzene ring, two CH₂-(H) and CH₂-(H') groups at 3-position, and N-(CH₂)ₚ-R substituent; Z on C-2.

| Ex. No. | X | Y | R | V | W | p | —(H) | —(H') | Z | m.p. °C. |
|---|---|---|---|---|---|---|---|---|---|---|
| 5 | H | H | CH₃ | — | — | 0 | 4-pyridyl | 4-pyridyl | O | 274–275 (2 HCl) 149.5–150.9 (free base) |
| 6 | H | H | phenyl(V,W) | 3-Cl | H | 0 | 4-pyridyl | 4-pyridyl | O | 275–276 (2 HCl) |
| 7 | H | H | phenyl(V,W) | H | H | 0 | 4-pyridyl N→O | 4-pyridyl N→O | O | 265.3–265.7 |
| 8 | H | H | phenyl(V,W) | H | H | 0 | 4-pyridyl | 4-pyridyl N→O | O | 217.7–218.5 |
| 9 | H | H | 4-pyridyl | — | — | 1 | 4-pyridyl | 4-pyridyl | O | 173–174 (3 HCl) |
| 10 | H | H | phenyl(V,W) | H | H | 0 | 2-pyridyl N→O | 2-pyridyl N→O | O | 196.1–196.7 |
| 11 | H | H | phenyl(V,W) | H | H | 0 | 3-pyridyl N→O | 3-pyridyl N→O | O | 201.7–202.0 |
| 12 | H | H | phenyl(V,W) | H | H | 0 | 2-pyridyl N→O | 2-pyridyl | O | Amorphous |

TABLE 1-continued

| Ex. No. | X | Y | R | V | W | p | —(H) | —(H) | Z | m.p. °C. |
|---|---|---|---|---|---|---|---|---|---|---|
| 13 | H | H | phenyl (V,W) | H | H | 0 | 3-pyridyl N-oxide | 3-pyridyl | O | Amorphous |
| 14 | H | H | phenyl (V,W) | H | H | 0 | 4-pyridyl | 4-pyridyl | S | |
| 15 | H | H | phenyl (V,W) | H | H | 0 | 2-Cl-5-pyridyl | 2-Cl-5-pyridyl | O | 230.8–231.4 |
| 16 | H | H | CH₃CH₂CH₂— | — | — | 0 | 4-pyridyl | 4-pyridyl | O | 227–228 (2 HCl) |
| 17 | H | H | phenyl (V,W) | H | H | 0 | 2-Cl-4-pyridyl | 2-Cl-4-pyridyl | O | |
| 18 | H | H | phenyl (V,W) | H | H | 0 | 2-CH₃-4-pyridyl | 2-CH₃-4-pyridyl | O | |
| 19 | 6-CH₃ | H | phenyl (V,W) | H | H | 0 | 4-pyridyl | 4-pyridyl | O | 217–219 |
| 20 | 6-OCH₃ | H | phenyl (V,W) | H | H | 0 | 4-pyridyl | 4-pyridyl | O | |
| 21 | 5-Cl | H | phenyl (V,W) | H | H | 0 | 4-pyridyl | 4-pyridyl | O | |

TABLE 1-continued
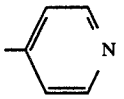
| Ex. No. | X | Y | R | V | W | p | —Ⓗ | —Ⓗ | Z | m.p. °C. |
|---|---|---|---|---|---|---|---|---|---|---|
| 22 | H | H | S | — | — | 0 | 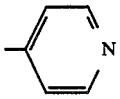 | 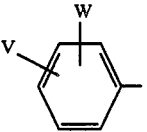 | O | |
| 23 | H | H | 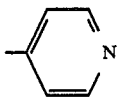 | H | H | 1 | 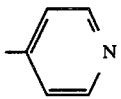 | 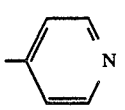 | O | |
| 24 | H | H | C₂H₅ | — | — | 0 | 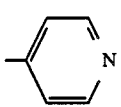 | 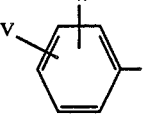 | O | |
| 25 | H | 7-NHC₃H₇ |  | H | H | 0 | 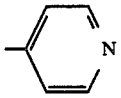 | 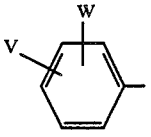 | O | |
| 26 | H | H |  | H | H | 0 | 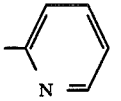 | 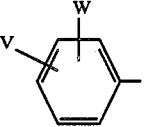 | S | |
| 27 | H | H | 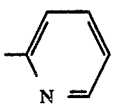 | 4-OCH₃ | 3-OCH₃ | 0 | 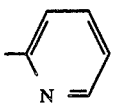 | 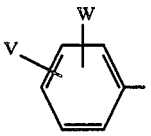 | O | |
| 28 | 5-OCH₃ | 6-OCH₃ | 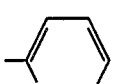 | H | H | 0 | 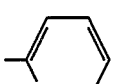 | 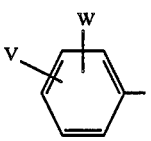 | O | |
| 29 | H | H | 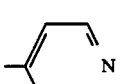 | 3-Cl | 4-Cl | 1 | 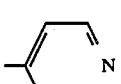 | 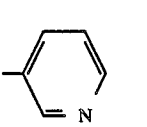 | O | |
| 30 | H | H | 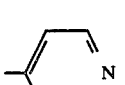 | — | — | 1 | 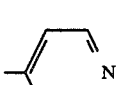 | 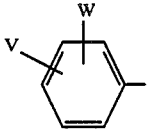 | O | |
| 31 | H | H | 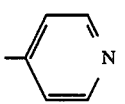 | 2-NO₂ | H | 0 | 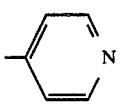 | | O | |

TABLE 1-continued
| Ex. No. | X | Y | R | V | W | p | —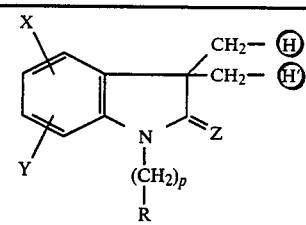 | —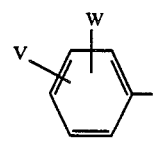 | Z | m.p. °C. |
|---|---|---|---|---|---|---|---|---|---|---|
| 32 | H | H | n-C₁₀H₂₁ | — | — | 1 | 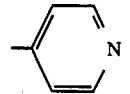 | 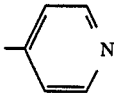 | O | |
| 33 | 5-CH₃ | 4-CH₃ | 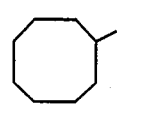 | H | H | 0 | 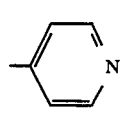 | 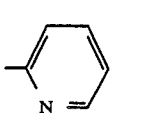 | S | |
| 34 | 4-NO₂ | H | 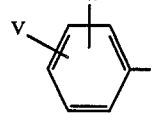 | — | — | 1 | 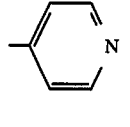 | 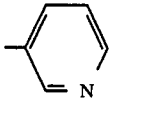 | O | |
| 35 | 4-N(CH₃)₂ | H | 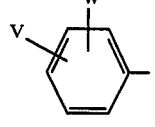 | H | 4-CF₃ | 0 | 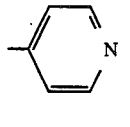 | 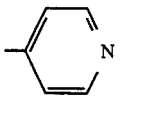 | O | |
| 36 | H | H | 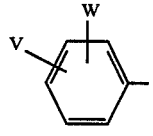 | H | 4-CN | 0 | 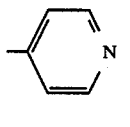 | 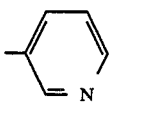 | O | |
| 37 | H | H | 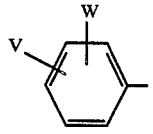 | H | 4-CF₃ | 1 | 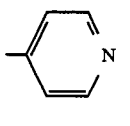 | 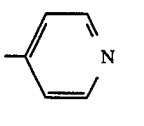 | O | |
| 38 | H | H | 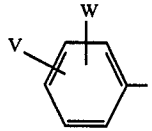 | H | 3-N(C₂H₅)₂ | 0 | 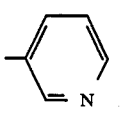 | 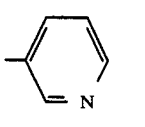 | O | |
| 39 | H | H | 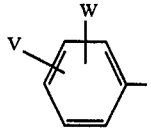 | H | H | 0 | 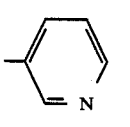 | 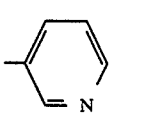 | S | |
| 40 | H | H | 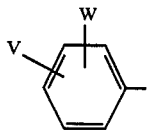 | 3-Cl | 4-Cl | 0 | 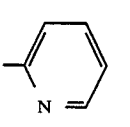 | 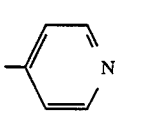 | O | |
| 41 | H | 4-CF₃ |  | H | H | 0 |  |  | O | |

TABLE 1-continued

[Structure: indoline derivative with X, Y substituents on benzene ring, N-(CH₂)ₚ-R group, =Z, and two CH₂-Ⓗ groups at the 3-position]

| Ex. No. | X | Y | R | V | W | p | —Ⓗ | —Ⓗ | Z | m.p. °C. |
|---|---|---|---|---|---|---|---|---|---|---|
| 42 | 5-N(CH₃)(C₂H₅) | H | cyclopropyl | — | — | 1 | 4-pyridyl | 4-pyridyl | O | |
| 43 | H | H | phenyl (V,W) | H | H | 0 | 4-pyridyl | pyrimidinyl | O | 167.5–169 |
| 44 | H | H | phenyl (V,W) | 3-NO₂ | H | 0 | 4-pyridyl | 4-pyridyl | S | |
| 45 | H | H | phenyl (V,W) | H | H | 0 | pyrazinyl | pyrazinyl | O | 123–124 |
| 46 | H | H | phenyl (V,W) | H | H | 0 | pyrimidinyl | pyrimidinyl | O | 152 |
| 47 | H | H | phenyl (V,W) | 4-CN | H | 0 | pyridazinyl | pyridazinyl | O | |
| 48 | 5-OC₂H₅ | H | phenyl (V,W) | H | H | 0 | chloro-methyl-pyridazinyl | chloro-methyl-pyridazinyl | O | |
| 49 | H | H | phenyl (V,W) | H | H | 0 | pyridazinyl | pyridazinyl | O | 233–235 |
| 50 | H | H | phenyl (V,W) | H | H | 0 | 4-amino-pyrimidinyl | 4-amino-pyrimidinyl | O | |

TABLE 1-continued

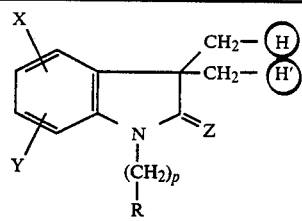

| Ex. No. | X | Y | R | V | W | p | —(H) | —(H') | Z | m.p. °C. |
|---|---|---|---|---|---|---|---|---|---|---|
| 51 | H | H | phenyl(V,W) | H | H | 0 | 5-methyl-4-pyrimidinyl | 5-methyl-4-pyrimidinyl | O | |
| 52 | H | H | phenyl(V,W) | H | H | 0 | 3-chloro-pyridazinyl | 3-chloro-pyridazinyl | O | |
| 53 | H | H | phenyl(V,W) | H | H | 0 | 3-methoxy-pyridazinyl | 3-methoxy-pyridazinyl | O | |
| 54 | H | H | phenyl(V,W) | H | H | 0 | 4-pyridyl | 4-pyrimidinyl | O | 131–133 |
| 55 | H | H | phenyl(V,W) | H | H | 0 | 4-pyridyl | 5-pyrimidinyl | O | |
| 56 | H | H | phenyl(V,W) | H | H | 0 | 4-pyridyl | 2-pyrimidinyl | O | |
| 57 | H | H | phenyl(V,W) | H | H | 0 | 4-pyridyl | 1,3,5-triazinyl | O | |
| 58 | H | H | phenyl(V,W) | H | H | 0 | 4-pyridyl | 3-pyridazinyl | O | |
| 59 | H | H | phenyl(V,W) | H | H | 0 | 4-pyridyl | 4-pyridazinyl | O | |

TABLE 1-continued

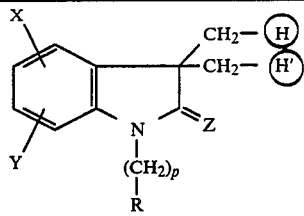

| Ex. No. | X | Y | R | V | W | p | —(H) | —(H') | Z | m.p. °C. |
|---|---|---|---|---|---|---|---|---|---|---|
| 60 | H | H | | — | — | 1 | | | | O |

Biochemical Test Procedure

The effect of compounds on the release of acetylcholine (ACh) from rat cerebral cortex slices was tested essentially using a slice superfusion procedure described by Mulder et al, Brain Res., 70, 372, (1974), as modified according to Nickolson et al, Naunyn Schmied. Arch. Pharmacol., 319, 48 (1982).

Male Wistar rats (Charles River) weighing 175-200 grams were used. They were housed for at least seven days before the experimentation in the animal facility under a 12-12 hour light/dark cycle (light on 6.00 h, light off 18.00 h). They had ad lib access to standard rat chow (Purina) and deionized water.

Rats were decapitated and brains were dissected immediately. Slices (0.3 mm thick) from the parietal cortex were prepared manually using a recessed Lucite ® guide and subsequently cut into 0.25×0.25 mm squares.

Slices (approximately 100 mg wet weight) were incubated in 10 ml Krebs-Ringer (KR) medium containing (mM): NaCl (116), KCl (3), $CaCl_2$ (1.3), $MgCl_2$ (1.2), $KH_2PO_4$ (1.2), $Na_2SO_4$ (1.2), $NaHCO_3$ (25), glucose (11), to which 10 μCi ³H-Choline (spec. act. approx. 35 Ci/mmol; NEN) and 10 nmoles unlabelled choline had been added to give a final concentration of $10^{-6}$M. Incubation was carried out for 30 minutes at 37° C. under a steady flow of 95% $O_2$/5% $CO_2$. Under these conditions, part of the radioactive choline taken up is converted into radioactive ACh by cholinergic nerve endings, stored in synaptic vesicles and released upon depolarization by high-$K^+$-containing media.

After labelling of the ACh stores, the slices were washed 3 times with non-radioactive KR-medium and transferred to a superfusion apparatus to measure the drug effects on ACh release. The superfusion apparatus consisted of 10 thermostated glass columns of 5 mm diameter which were provided with GF/F glass fiber filters to support the slices (approximately 10 mg tissue/column). Superfusion was carried out with KR-medium (0.3 ml/min) containing $10^{-5}$M hemicholinium-3 (HC-3). HC-3 prevents the uptake of choline, formed during the superfusion from phospholipids and released ACh, which would be converted into unlabelled ACh, and released in preference to the preformed, labelled ACh. The medium was delivered by a 25-channel peristaltic pump (Ismatec; Brinkman) and was warmed to 37° C. in a thermostated stainless steel coil before entering the superfusion column. Each column was provided with a 4-way slider valve (Beckman Instruments) which allowed rapid change of low- to high-$K^+$-KR-medium and with two 10-channel, 3-way valves which were used to change from drug-free to drug-containing low- and high-$K^+$-KR-medium.

After 15 minutes washout of non-specifically bound radioactivity, the collection of 4 minute fractions were started. After 3 four-min. collections, the KR medium was changed for KR medium of which the KCl concentration had been increased to 25 mM (high-$K^+$-KR-medium) (S1). Depolarization-induced stimulation of release by high-$K^+$-KR-medium lasted for 4 minutes. Drug free low- and high-$K^+$-KR-medium were then substituted by drug- or vehicle-containing low- and high-$K^+$-KR-medium and superfusion was continued for 3 four-min. collections with low-$K^+$-KR-medium, 1 four-min. collection with high-$K^+$-KR-medium (S2) and 2 four-min. collections with low-$K^+$-KR-medium.

Drug was added to the media by 100-fold dilution of appropriate concentrations of the drug (in 0.9% NaCl/$H_2O$) with either low- or high-$K^+$-KR-medium.

All superfusion fractions were collected in liquid scintillation counting vials. After superfusion the slices were removed from the superfusion columns and extracted in 1.0 ml of 0.1N HCl. To superfusion fractions and extracts 12 ml Liquiscint counting fluid (NEN) was then added and samples were counted in a Packard Tricarb Liquid Scintillation Counter. No corrections were made for quenching.

The ratio of S2/S1 (as compared to controls where no drug is present during S2) is a measure of the ability of the drug to enhance or depress stimulus-induced acetylcholine release. The in vitro ACh release data is summarized in Table 2.

TABLE 2

% INCREASE OF STIMULUS-INDUCED ACh RELEASE IN RAT CEREBRAL CORTEX IN VITRO

| Example | $10^{-6}$ | $10^{-5}$ | $10^{-4}$ (M) |
|---|---|---|---|
| 1 | — | — | +349* |
| 2 | +11 | +61* | +265* |
| 3 | +06 | +88* | +238* |
| 4 | +94* | +457* | +433* |
| 5 | +14 | +78* | +355* |
| 6 | +195* | +313* | — |
| 7 | — | 0 | +30* |
| 8 | — | +37* | +429* |
| 9 | 0 | +54* | +275* |
| 12 | — | +11 | +48* |
| 13 | 0 | +13 | +100* |
| 16 | +01 | +47* | — |
| 19 | +34* | +323* | — |
| 43 | +34* | +210* | — |
| 45 | — | +12 | +97* |

TABLE 2-continued

| % INCREASE OF STIMULUS-INDUCED ACh RELEASE IN RAT CEREBRAL CORTEX IN VITRO | | | |
|---|---|---|---|
| Example | $10^{-6}$ | $10^{-5}$ | $10^{-4}$ (M) |
| 46 | +20 | +218* | — |
| 49 | +16* | +49* | — |

*Significantly different from control P < 0.05, student's t-test.

Using similar test procedures, the compounds of Examples 2 and 4 were also found to enhance the release of acetylcholine from hippocampal slices and that of acetylcholine and dopamine from caudate nucleus slices in vitro. The compound of Example 4, in addition, was found to also enhance the release of serotonin from cortical slices.

Behavioral Test Procedure

The effect of compounds on rat active avoidance (pole-climb) performance was studied as follows: Male Sprague-Dawley rats (Charles River), weighing 150–200 grams, received two blocks of learning trials daily (1 AM, 1 PM), for four days. A trial consisted of placing a rate in a cage (Coulbourn Model E10-10, equipped with a removal shock gridfloor), facing a pole (wood, with parallel diagonal notches, mounted from the ceiling). The trial was started by closing the cage door and switching on the cage light. After 10 seconds, shock was applied through the gridfloor for 10 seconds by a Coulbourn Model E13-08 shocker. Footshock intensity ranged from 0.6 to 1.2 mA. At the end of the trial, the light and shock were turned off and the rat was removed from the cage. If the rat jumped on the pole prior to the onset of shock, it was considered to have avoided; if it jumped after the shock, it was considered to have escaped. Groups of 6 to 9 rats were subcutaneously treated with various doses of a compound or the corresponding vehicle 30 minutes prior to the first training trial of each block.

Active avoidance performance data were analyzed by regression analysis (see Snedecor and Cochran, *Statistical Methods*, 6th Edition, page 432) of the cumulative number of avoidances versus blocks of trials curve. The mean slope and SEM (Standard Error of the Mean) of this curve were calculated for each treatment group and taken as a measure of active avoidance performance. Drug effects were expressed as percent change in slope compared to the slope of the control curve. The results are summarized in Table 3.

TABLE 3

| % ENHANCEMENT OF ACTIVE AVOIDANCE PERFORMANCE IN RATS | | | | | | | |
|---|---|---|---|---|---|---|---|
| | Drug Dose (mg/kg s.c.) | | | | | | |
| Example | 0.1 | 0.3 | 1 | 3 | 5 | 10 | 20 |
| 2 | — | — | — | — | 54* | 53* | 21 |
| 4 | +59* | +91* | +84* | +57 | — | — | — |

*Significantly different from control, P < 0.05, student's t-test.

Utility

The foregoing test results suggest that compounds of this invention have utility in the treatment of cognitive deficiencies and/or neurological function deficits and/or mood and mental disturbances, in patients suffering from nervous system disorders like Alzheimer's disease, Parkinson's disease, senile-dementia, multi-infarct dementia, Huntington's disease, mental retardation, Myasthenia Gravis etc. Compounds of this invention can be administered to treat said deficiencies by any means that produces contact of the active agent with the agent's site of action in the body of a mammal. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of said diseases, a daily oral dosage of active ingredient can be about 0.001 to 100 mg/kg of body weight. Ordinarily a dose of 0.01 to 10 mg/kg per day in divided doses one to four times a day or in sustained release form is effective to obtain the desired results.

Dosage forms (compositions) suitable for administration contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

What is claimed is:

1. A pharmaceutical composition comprising a suitable pharmaceutical carrier and an amount effective to treat cognitive or neurological dysfunction of a compound having the formula:

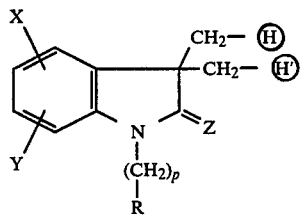

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl, or

V, W, X, and Y independently are H, halo, $C_1$-$C_3$ alkyl, $OR^1$, $NO_2$, $CF_3$, CN or $NR^1R^2$;
$R^1$ and $R^2$ independently are H or $C_1$-$C_3$ alkyl; —(H) and —(H') independently are 6-membered heterocyclic aromatic rings containing one nitrogen atom as a part of the ring optionally substituted with one substituent selected from the group $C_1$-$C_3$ alkyl, halo, $OR^1$ or $NR^1R^2$; or an N-oxide or pharmaceutically suitable acid addition salt thereof.

2. A composition of claim 1 wherein p is 0.
3. A composition of claim 1 wherein Z is O.
4. A composition of claim 1 wherein each of X and Y is H.
5. A composition of claim 1 wherein R is $CH_3$, phenyl, or m-chlorophenyl.
6. A composition of claim 1 wherein each of —(H) and —(H') is pyridyl attached by a ring carbon atom.
7. A composition of claim 1 wherein:
p is 0; Z is O; each of X and Y is H; R is $CH_3$, m-chlorophenyl or phenyl; and each of —(H) and —(H') is pyridyl attached by a ring carbon.
8. A composition of claim 1 wherein the compound is 3,3-bis(2-pyridylmethyl)-1-phenylindolin-2-one or a pharmaceutically suitable acid addition salt thereof.
9. A composition of claim 1 wherein the compound is 3,3-bis(3-pyridylmethyl)-1-phenylindolin-2-one or a pharmaceutically suitable acid addition salt thereof.
10. A composition of claim 1 wherein the compound is 3,3-bis(4-pyridylmethyl)-1-phenylindolin-2-one or a pharmaceutically suitable acid addition salt thereof.
11. A composition of claim 1 wherein the compound is 3,3-bis(4-pyridylmethyl)-1-methylindoline-2-one or a pharmaceutically suitable acid addition salt thereof.
12. A composition of claim 1 wherein the compound is 3,3-bis(4-pyridylmethyl)-1-(3-chlorophenyl)-indolin-2-one or a pharmaceutically suitable acid addition salt thereof.
13. A method for the treatment of cognitive or neurological dysfunction in a mammal comprising administering to the mammal a therapeutically effective amount of a compound of the formula:

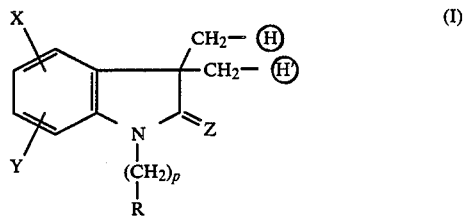

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl, or

V, W, X, and Y independently are H, halo, $C_1$-$C_3$ alkyl, $OR^1$, $NO_2$, $CF_3$, CN or $NR^1R^2$;
$R^1$ and $R^2$ independently are H or $C_1$-$C_3$ alkyl; —(H) and —(H) independently are 6-membered heterocyclic aromatic rings containing one nitrogen, atom as part of the ring optionally substituted with one substituent selected from the group $C_1$-$C_3$ alkyl, halo, $OR^1$ or $NR^1R^2$; or an N-oxide or pharmaceutically suitable acid addition salt thereof.

14. A method of claim 13 wherein p is 0.

15. A method of claim 13 wherein Z is O.

16. A method of claim 13 wherein each of X and Y is H.

17. A method of claim 13 wherein R is $CH_3$, phenyl, or m-chlorophenyl.

18. A method of claim 13 wherein each of —Ⓗ and —Ⓗ' is pyridyl attached by a ring carbon atom.

19. A method of claim 13 wherein:
p is 0; Z is O; each of X and Y is H; R is $CH_3$, phenyl or m-chlorophenyl; and each of —Ⓗ and —Ⓗ' is pyridyl attached by a ring carbon.

20. A method of claim 13 wherein the compound is 3,3-bis(2-pyridylmethyl)-1-phenylindolin-2-one or a pharmaceutically suitable acid addition salt thereof.

21. A method of claim 13 wherein the compound is 3,3-bis(3-pyridylmethyl)-1-phenylindolin-2-one or a pharmaceutically suitable acid addition salt thereof.

22. A method of claim 13 wherein the compound is 3,3-bis(4-pyridylmethyl)-1-phenylindolin-2-one or a pharmaceutically suitable acid addition salt thereof.

23. A method of claim 13 wherein the compound is 3,3-bis(4-pyridylmethyl)-1-methylindolin-2-one or a pharmaceutically suitable acid addition salt thereof.

24. A method of claim 13 wherein the compound is 3,3-bis(4-pyridylmethyl)-1-(3-chlorophenyl)indolin-2-one or a pharmaceutically suitable acid addition salt thereof.

25. A compound having the formula:

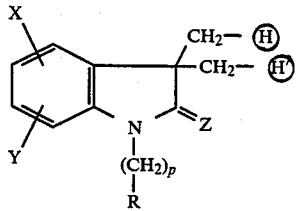

(I)

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl, or

;

V, W, X, and Y independently are H, halo, $C_1$-$C_3$ alkyl, $OR^1$, $NO_2$, $CF_3$, CN or $NR^1R^2$;

$R^1$ and $R^2$ independently are H or $C_1$-$C_3$ alkyl;

—Ⓗ and —Ⓗ' independently are 6-membered heterocyclic aromatic rings containing one nitrogen atom as a part of the ring optionally substituted with one substituent selected from the group $C_1$-$C_3$ alkyl, halo, $OR^1$ or $NR^1R^2$; or an N-oxide or pharmaceutically suitable acid addition salt thereof.

26. A compound of claim 25 wherein p is 0.

27. A compound of claim 25 wherein Z is O.

28. A compound of claim 25 wherein each of X and Y is H.

29. A compound of claim 25 wherein R is $CH_3$, phenyl or m-chlorophenyl.

30. A compound of claim 25 wherein each of —H and —H' is pyridyl attached by a ring carbon atom.

31. A compound of claim 25 wherein:
p is 0; Z is O; each of X and Y is H; R is $CH_3$, phenyl or m-chlorophenyl; and each of —Ⓗ and —Ⓗ' is pyridyl attached by a ring carbon.

32. The compound of claim 25 which is 3,3-bis(2-pyridylmethyl)-1-phenylindolin-2-one or a pharmaceutically suitable acid addition salt thereof.

33. The compound of claim 25 which is 3,3-bis(3-pyridylmethyl)-1-phenylindolin-2-one or a pharmaceutically suitable acid addition salt thereof.

34. The compound of claim 25 which is 3,3-bis(4-pyridylmethyl)-1-phenylindolin-2-one or a pharmaceutically suitable acid addition salt thereof.

35. The compound of claim 25 which is 3,3-bis(4-pyridylmethyl)-1-methylindolin-2-one or a pharmaceutically suitable acid addition salt thereof.

36. The compound of claim 25 which is 3,3-bis(4-pyridylmethyl)-1-(3-chlorophenyl)indolin-2-one or a pharmaceutically suitable acid addition salt thereof.

* * * * *